United States Patent [19]

Moore, Jr.

[11] 3,987,025

[45] Oct. 19, 1976

[54] LIQUID AZONITRILE MIXTURES

[75] Inventor: Earl P. Moore, Jr., Hockessin, Del.

[73] Assignee: E. I. Du Pont de Nemours and Company, Wilmington, Del.

[22] Filed: June 28, 1974

[21] Appl. No.: 484,309

[52] U.S. Cl. ............................. 260/192; 252/186; 252/350; 260/80 R; 260/88.3 R; 260/88.7 R; 260/89.3; 260/89.5 A; 260/92.8 R; 260/93.1; 260/93.5 R; 260/465.5 R; 526/218; 526/260; 526/263; 526/291; 526/317; 526/328; 526/330; 526/341; 526/343; 526/344; 526/348; 526/352

[51] Int. Cl.$^2$ ........................................ C07C 107/02

[58] Field of Search ........................... 260/192, 152

[56] References Cited

UNITED STATES PATENTS

| | | | |
|---|---|---|---|
| 2,471,959 | 5/1949 | Hunt | 260/89.5 |
| 2,565,573 | 8/1951 | Pease et al. | 260/192 |
| 2,711,405 | 6/1955 | Anderson | 260/192 |
| 2,713,576 | 7/1955 | De Benneville | 260/192 |
| 3,170,913 | 2/1965 | De Benneville et al. | 260/192 |
| 3,268,506 | 8/1966 | De Vries | 260/192 |
| 3,390,146 | 6/1968 | Nield et al. | 260/192 |
| 3,775,395 | 11/1973 | Koyanagi et al. | 260/192 |
| 3,783,148 | 1/1974 | Fuchs | 260/192 |

Primary Examiner—Floyd D. Higel

[57] ABSTRACT

Liquid mixtures of symmetrical and asymmetrical azonitriles are provided which have a maximum freezing point of 25° C. including mixtures of:

A. 2,2'-azobis(2-methylbutyronitrile), 2,2'-azobis(2-methylhexanonitrile) and 2-[(1-cyano-1-methylpropyl)azo]-2-methylhexanonitrile;

B. 2,2-azobis(2-methylbutyronitrile), 2,2'-azobis(2-methylheptanonitrile) and 2-[(1-cyano-1-methylpropyl)azo]-2-methylheptanonitrile;

C. 2,2'-azobis(2-methylbutyronitrile), 2,2'-azobis(2-ethylhexanonitrile) and 2-[(1-cyano-1-methylpropyl)azo]-2-ethylhexanonitrile;

D. 2,2'-azobis(2-methylbutyronitrile), 2,2'-azobis(2-ethylheptanonitrile) and 2-[(1-cyano-1-methylpropyl)azo]-2-ethylheptanonitrile;

E. 2,2'-azobis(2-methylbutyronitrile), 2,2'-azobis(2-methyloctanonitrile) and 2-[(1-cyano-1-methylpropyl)azo]-2-methyloctanonitrile;

F. 2,2'-azobis(2-methylpentanonitrile), 2,2'-azobis(2-ethylhexanonitrile) and 2-[(1-cyano-1-methylbutyl)azo]-2-ethylhexanonitrile;

G. 2,2'-azobis(2-methylhexanonitrile), 2,2'-azobis(2-methyloctanonitrile) and 2-[(1-cyano-1-methylpentyl)azo]-2-methyloctanonitrile;

H. 2,2'-azobis(2-methylpentanonitrile), 2,2'-azobis(2-ethylheptanonitrile) and 2-[(1-cyano-1-methylbutyl)azo]-2-ethylheptanonitrile;

I. 2,2'-azobis(2-methylhexanonitrile, 2,2'-azobis(2-methylheptanonitrile) and 2-[(1-cyano-1-methylpentyl)azo]-2-methylheptanonitrile;

J. 2,2'-azobis(2-methylpentanonitrile), 2,2'-azobis(2-methyloctanonitrile) and 2-[(1-cyano-1-methylbutyl)azo]-2-methyloctanonitrile;

K. 2,2'-azobis(2-methylpentanonitrile), 2,2'-azobis(2-methylhexanonitrile) and 2-[(1-cyano-1-methylbutyl)azo]-2-methylhexanonitrile;

L. 2,2'-azobis(2-methylpentanonitrile), 2,2'-azobis(2-methylheptanonitrile) and 2-[(1-cyano-1-methylbutyl)azo]-2-methylheptanonitrile; and M. 2,2'-azobis(2-methylhexanonitrile), 2,2'-azobis(2-ethylheptanonitrile) and 2-[(1-cyano-1-methylpentyl)azo]-2-ethylheptanonitrile.

The above liquid mixtures are useful as polymerization initiators in high pressure polymerization reactions.

4 Claims, No Drawings

LIQUID AZONITRILE MIXTURES

BACKGROUND OF THE INVENTION

Azonitrile compounds are known to be useful as polymerization initiators. They are advantageous because they can be used with a higher degree of safety than peroxide catalysts and yield both performance and economic improvements over other catalysts which might be used in the same type of polymerization reaction.

Symmetrical azonitrile compounds are generally solid and have low solubility in many organic solvents, especially non-polar types, particularly at high pressures (15,000 p.s.i. and higher). Asymmetrical azonitrile compounds, on the other hand, usually have appreciably lower melting points than symmetrical azonitriles. Many asymmetrical azonitriles are liquids at room temperature and below and all tend to have much higher solubility in organic liquids. Producers of low density polyethylene have been seeking efficient and effective liquid azo polymerization catalysts for many years. While compounds such as 2,2'-azobis-(isobutyronitrile) are highly effective as initiators in the production of low density polyethylene, this material is a solid which cannot be handled in the process equipment except in solution form. Under the conditions employed for the polymerization, such as, for example, elevated pressure, solid azonitriles crystallize from solution and plug the equipment. Liquid azonitriles which are as active as 2,2'-azobis(isobutyronitrile) and which have freezing points of 0° C. or lower, preferably −20° C. or lower, would be ideal for the production of low density polyethylene which is carried out at pressures of from about 15,000 to about 50,000 p.s.i.

The only published process for producing asymmetrical liquid azonitrile initiators involves a reaction scheme utilizing t-butylhydrazine and a ketone as reagents to which is added HCN. As described in Canadian Pat. No. 924,299 issued to Ronald E. MacLeay et al. on Apr. 10, 1973, upon oxidation, the following compounds are obtained

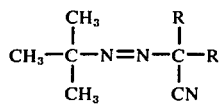

Such a process is costly because it is lengthy and requires the use of t-butylhydrazine which is not a common chemical. Further, compounds containing the nitrile group at both ends are not obtained by this process.

SUMMARY OF THE INVENTION

It has now been found that liquid mixtures of azonitriles having a maximum freezing point of 25° C., particularly 0° C., and most particularly −20° C., and comprising mixtures of symmetrical and asymmetrical azonitrile compounds can be obtained from a two-aminonitrile system as outlined in the following reaction sequence:

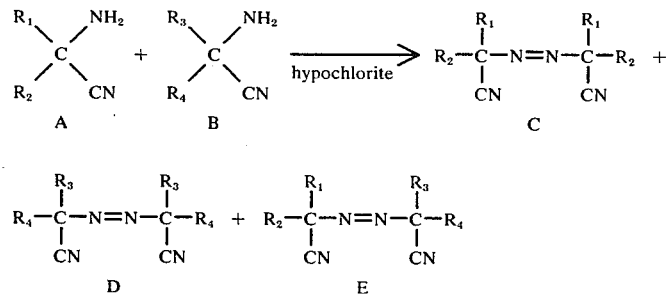

when A is 2-amino-2-methylbutyronitrile and B is 2-amino-2-methylhexanonitrile, 2-amino-2-methylheptanonitrile, 2-amino-2-methyloctanonitrile, 2-amino-2-ethylhexanonitrile or 2-amino-2-ethylheptanonitrile or when A is 2-amino-2-methylpentanonitrile and B is 2-amino-2-methylhexanonitrile, 2-amino-2-methylheptanonitrile, 2-amino-2-methyloctanonitrile, 2-amino-2-ethylhexanonitrile or 2-amino-2-ethylheptanonitrile or A is 2-amino-2-methylhexanonitrile and B is 2-amino-2-methylheptanonitrile, 2-amino-2-methyloctanonitrile or 2-amino-2-ethylheptanonitrile. A and B are reacted at molar ratios ranging from 2.5:1 to 1:2.5 depending on the specific compounds involved in the reaction as discussed hereinafter. C and D are symmetrical azonitriles and E is an unsymmetrical azonitrile.

The most particularly preferred azonitrile mixtures of this invention include I
A. 2,2'-azobis(2-methylbutyronitrile),
  2,2'-azobis(2-methylhexanonitrile) and
  2-[(1-cyano-1-methylpropyl)azo]-2-methylhexanonitrile prepared from
  2-amino-2-methylbutyronitrile and
  2-amino-2-methylhexanonitrile;
B. 2,2-azobis(2-methylbutyronitrile),
  2,2'-azobis(2-methylheptanonitrile) and
  2-[(1-cyano-1-methylpropyl)azo]-2-methylheptanonitrile prepared from
  2-amino-2-methylbutyronitrile and
  2-amino-2-methylheptanonitrile, and
C. 2,2'-azobis(2-methylbutyronitrile),
  2,2'-azobis(2-ethylhexanonitrile) and
  2-[(1-cyano-1-methylpropyl)azo]-2-ethylhexanonitrile prepared from
  2-amino-2-methylbutyronitrile and
  2-amino-2-ethylhexanonitrile;
D. 2,2'-azobis(2-methylbutyronitrile),
  2,2'-azobis(2-ethylheptanonitrile) and
  2-[(1-cyano-1-methylpropyl)azo]-2-ethylheptanonitrile prepared from
  2-amino-2-methylbutyronitrile and
  2-amino-2-ethylheptanonitrile.

Preferred azonitrile mixtures of this invention include II
E. 2,2'-azobis(2-methylbutyronitrile),
  2,2'-azobis(2-methyloctanonitrile) and 2-[(1-cyano-1-methylpropyl)azo]-2-methyloctanonitrile prepared from
2-amino-2-methylbutyronitrile and
2-amino-2-methyloctanonitrile;
F. 2,2'-azobis(2-methylpentanonitrile),
2,2'-azobis(2-ethylhexanonitrile) and
2-[(1-cyano-1-methylbutyl)azo]-2-ethylhexanonitrile prepared from
2-amino-2-methylpentanonitrile and
2-amino-2-ethylhexanonitrile and
G. 2,2'-azobis(2-methylhexanonitrile),
2,2'-azobis(2-methyloctanonitrile), and
2-[(1-cyano-1-methylpentyl)azo]-2-methyloctanonitrile prepared from
2-amino-2-methylhexanonitrile, and
2-amino-2-methyloctanonitrile;
H. 2,2'-azobis(2-methylpentanonitrile),
2,2'-azobis(2-ethylheptanonitrile) and
2-[(1-cyano-1-methylbutyl)azo]-2-ethylheptanonitrile prepared from
2-amino-2-methylpentanonitrile and
2-amino-2-ethylheptanonitrile.

A third category of important azonitrile mixtures of this invention includes III
I. 2,2'-azobis(2-methylhexanonitrile),
2,2'-azobis(2-methylheptanonitrile),
2-[(1-cyano-1-methylpentyl)azo]-2-methylheptanonitrile prepared from
2-amino-2-methylhexanonitrile and
2-amino-2-methylheptanonitrile;
J. 2,2'-azobis(2-methylpentanonitrile),
2,2'-azobis(2-methyloctanonitrile),
2-[(1-cyano-1-methylbutyl)azo]-2-methyloctanonitrile prepared from
2-amino-2-methylpentanonitrile and
2-amino-2-methyloctanonitrile;
K. 2,2'-azobis(2-methylpentanonitrile),
2,2'-azobis(2-methylhexanonitrile),
2-[(1-cyano-1-methylbutyl)azo]-2-methylhexanonitrile prepared from
2-amino-2-methylpentanonitrile and
2-amino-2-methylhexanonitrile;
L. 2,2'-azobis(2-methylpentanonitrile),
2,2'-azobis(2-methylheptanonitrile),
2-[(1-cyano-1-methylbutyl)azo]-2-methylheptanonitrile prepared from
2-amino-2-methylpentanonitrile and
2-amino-2-methylheptanonitrile;
M. 2,2'-azobis(2-methylhexanonitrile),
2,2'-azobis(2-ethylheptanonitrile) and 2[(1-cyano-1-methylpentyl)azo]-2-ethylheptanonitrile prepared from
2-amino-2-methylhexanonitrile and
2-amino-2-ethylheptanonitrile.

DETAILED DESCRIPTION OF THE INVENTION

Only aminonitriles A and B having unbranched hydrocarbon groups as part of their structure can be used to prepare the azonitrile mixtures of this invention. When aminonitriles having branched hydrocarbon groups are employed, solid azonitrile mixtures are obtained. The most preferred azonitrile mixtures of this invention are prepared from molar ratios of A and B of 1:1 yield the theoretical molar ratio of C:D:E of 1:1:2. A change in the molar ratio of A to B will increase the melting point of the final azonitrile mixture. The degree of variation from the 1:1 molar ratio which is acceptable varies depending on the particular reactants employed. For example, when 2-amino-2-methylbutyronitrile A is reacted with 2-amino-2-methylhexanonitrile, 2-amino-2-methylheptanonitrile, 2-amino-2-ethylhexanonitrile or 2-amino-2-ethylheptanonitrile B the molar ratio of A to B can vary from 2.5:1 to 1:2.5. When 2-amino-2-methylbutyronitrile, 2-amino-2-methylhexanonitrile, or 2-amino-2-methylpentanonitrile A are reacted with 2-amino-2-methyloctanonitrile, 2-amino-2-methyloctanonitrile or 2-amino-2-ethylhexanonitrile B, respectively, or 2-amino-2-methylpentanonitrile A is reacted with 2-amino-2-ethylheptanonitrile B, the molar ratio of A to B can vary from 1.5:1 to 1:1.5. When 2-amino-2-methylhexanonitrile A is reacted with 2-amino-2-methylheptanonitrile or 2-amino-2-ethylheptanonitrile B or when 2-amino-2-methylpentanonitrile A is reacted with 2-amino-2-methyloctanonitrile, 2-amino-2-methylhexanonitrile or 2-amino-2-methylheptanonitrile B the molar ratio of A to B can vary from 1.15:1 to 1:1.15. Theoretically, molar ratios A to B of 2.5:1 to 1:2.5 give mixtures of C:D:E of 6.3:1:5 to 1:6.3:5; molar ratios of A to B of 1.5:1 to 1:1.5 give mixtures of C:D:E of 2.3:1:3 to 1:2.3:3 and molar ratios of A to B of 1.15:1 to 1:1.15 give mixtures of C:D:E of 1.3:1:2.3 to 1:1.3:2.3. The azonitrile mixtures listed under I above are prepared from aminonitriles at a molar ratio of 2.5:1 to 1:2.5. The azonitrile mixtures listed under II above are prepared from aminonitriles at a molar ratio of 1.5:1 to 1:1.5. The azonitrile mixtures listed under III above are prepared from aminonitriles at a molar ratio of 1.15:1 to 1:1.15.

The azonitrile mixtures of this invention are generally liquid at from +25° C. to −30° C., the preferred mixtures being liquid at 0° C. with the most preferred being liquid at −20° C. Those mixtures which are still liquid at the lower temperatures are valuable where the use of a full strength initiator is desired. Mixtures of azonitriles which are liquid at from 25° C. (room temperature) down to about 0° C. but freeze before reaching 0° C. include those listed under III above. Preferred azonitrile mixtures which are liquid at from 0° C. down to about −20° C. but freeze before reaching −20° C. include those listed under II above. The most preferred azonitrile mixtures which are liquid at −20° C. and below, generally from −20° C. to −30° C., include those listed under I above.

The liquid azonitrile mixtures of this invention are useful in producing ethylene copolymers. High pressure copolymerizations of ethylene and vinyl acetate, methyl methacrylate, ethyl acrylate, acrylic and methacrylic acids and salts, vinyl chloride, acrylonitrile, olefins such as propylene, butene-1 and butadiene, dibutyl maleate, carbon monoxide, and the like can be carried out easily and efficiently using the azonitrile mixtures of this invention as polymerization initiators.

These new compositions are initiators for the polymerization or copolymerization of other unsaturated monomers such as alkenes, vinyl halides, vinyl esters, vinylidene halides, vinyl cyanides and alkenyl aromatics as well as curing agents for polyester resins, initiators for free radical initiated chemical reactions, blowing agents for producing foamed polymer and plastics and selective oxidizing agents.

Illustrative polymerizable monomers other than ethylene and ethylene-comonomers are vinyl chloride, vinylidene chloride, vinyl acetate, vinyl pyridine, vinyl pyrrolidone, vinyl carbazole, butadiene, isoprene, acrylonitrile, acrylic acid, acrylic acid esters, methacrylic acid, methacrylic acid esters, styrene, chlorostyrene and methyl styrenes.

The liquid azonitrile mixtures of this invention are concentrated fluids and are useful full strength where desirable, convenient or necessary. For example, low density polyethylene production may require very rapid introduction of full strength material into the reactor because of very high reactor speeds and throughput of monomer. In such cases, stable liquid behavior under 15,000 to 50,000 p.s.i. pressure is exceedingly important. Other polyethylene producers may desire less potent initiators and, in such cases, concentrations of from 10 to 85% by weight of the azonitrile mixtures of this invention in a suitable solvent are used.

Any organic solvent which is liquid under reaction conditions and inert with respect to the azonitriles of this invention may be used as a diluent for the azonitrile mixtures described herein. Some such suitable solvents include, for example, alcohols, preferably those having from one to eight carbon atoms such as methyl, ethyl, isopropyl, cyclohexyl and n-octyl alcohols and the like; aliphatic hydrocarbons having five to eight carbon atoms such as pentane, hexane, octane, cyclohexane and the like; esters having the formula $R_1COOR_2$ wherein $R_1$ has one to eight carbon atoms or is hydrogen and $R_2$ has one to eight carbon atoms or is $-(CH_2CH_2O)_{1-3}R$ wherein R has one to four carbon atoms such as methyl formate, ethyl acetate, butyl formate, 2-ethylhexyl octanoate, dimethylphthalate, ethylene glycol monoethyl ether acetate and the like; glycol ethers having the formula $HO(CH_2CH_2O)_{1-3}R$ wherein R is hydrogen or has one to four carbon atoms; ethers having four to ten carbon atoms such as ethyl ether, isopropyl ether, dioxane, tetrahydrofuran and the like; ketones having two to eight carbon atoms in addition to the carbonyl carbon such as acetone, cyclohexanone, methyl isobutyl ketone, 2-decanone and the like; aliphatic petroleum naphthas having five to twenty carbon atoms such as pentane, heptane, kerosene, mineral spirits, petroleum ethers, Stoddard solvents, odorless mineral spirits, VM&P naphtha and the like; aromatic hydrocarbons having six to ten carbon atoms such as benzene, toluene, xylene, pseudocumene and the like; chlorinated aliphatic hydrocarbons having one to six carbon atoms such as carbon tetrachloride, ethylene dichloride, perchloroethylene, methylene chloride, chloroform and the like; chlorinated aromatic hydrocarbons such as chlorobenzene, benzyl chloride and the like; amides having the formula

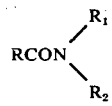

wherein R has one to four carbon atoms or is hydrogen, and $R_1$ and $R_2$ are the same or different methyl or ethyl group or hydrogen such as formamide, N,N-dimethylformamide, N,N-dimethylacetamide, N-methylacetamide, N-methyl-N-ethylformamide and the like; nitriles having the formula RCN wherein R has one to six carbon atoms such as acetonitrile, butyronitrile, benzonitrile and the like or mixtures of any of them. Instead of or in addition to the foregoing solvents, one may also use the monomer to be polymerized as described herein as the solvent for the azonitrile mixtures of this invention.

The aminonitriles used in preparing the azonitrile mixtures of this invention can be obtained from commercial sources or they can be prepared from aldehydes and ketones as described, for example, in U.S. Pat. Nos. 3,131,210 issued to Robert H. Uegell et al. on Apr. 28, 1964 and 3,541,132 issued to Richard N. Knowles on Nov. 17, 1960.

The hypochlorite can be sodium, potassium or calcium hypochlorite. The hypochlorite can be prepared first, then added to the reaction mixture or it can be prepared in situ by reacting chlorine and the appropriate hydroxide. For economy and convenience, sodium hypochlorite is preferred. The amount of the hypochlorite used is generally one mole per mole of the aminonitrile starting materials. However, if an alcoholic solvent is used, extra hypochlorite is required because side reactions take place between the hypochlorite and alcohol. For maximum efficiency in any case, it is preferred to use at least 1.2 moles of hypochlorite per mole of amino compound. Some yield loss occurs when more than 2.5 moles of the hypochlorite per mole of the amino compound are employed.

The solvent used in preparing the azonitrile mixtures is a $C_1$–$C_2$ alcohol, i.e., methanol or ethanol. At the beginning of the reaction, the alcohol constitutes at least 95 percent by volume of the reaction solvent; at the end of the reaction, the alcohol concentration should be at least 70 percent by volume. Some water usually is present in the reaction medium, for instance, as solvent for sodium hypochlorite. The amount of alcohol depends on the strength of the hypochlorite; stronger solutions require less alcoholic solvent, but in the presence of lower concentrations of alcohol the intermediate chloramines oil out, causing the yields to decrease appreciably.

It is believed that the outstanding results which are obtained when using the $C_1$–$C_2$ alcohol solvents are due to their high compatibility with the high ionic strength of the reaction medium (due to high levels of sodium chloride). This high compatibility results in the formation of only one liquid phase which in turn improves the rate of the desired reaction and simplifies isolation of the azo product. The alcohols methanol and ethanol can be used either singly or in combination with each other. The preferred alcohol is methanol.

In the following text, whenever the term "aqueous solvent" is used, it is understood that the solvent contains some water, and not that the water constitutes a major part thereof.

The reactants can be mixed in any suitable reaction vessel where they are agitated for a time sufficient for the reaction to go to completion. Ordinarily 60 minutes is a sufficient reaction time. In the broadest aspect of this invention, the hypochlorite solution is added to the solution of the amino compound in at least 95 percent by volume alcohol. Reverse order of addition, i.e., addition of the amino compound solution to the hypochlorite is detrimental to both the yield and purity of the resulting azo compound.

The lower operable temperature of the reaction is limited only by the freezing point of the reaction mixture and the difficulty and expanse of attaining and controlling the temperature. Generally, temperatures below −25° C. offer no advantage. The upper operable temperature of the reaction is circumscribed by the appearance of side reaction products such as chlorinated organic by-products which reduce the yield. Generally, a maximum of 0° C. should be observed if the formation of by-products is to be prevented.

Although the aminonitrile mixture [A + B] and the hypochlorite can be added separately to the alcohol, it is preferred that the addition be simultaneous since the heat load is more easily controlled. If the aminonitrile mixture is a liquid, it may most conveniently be added "neat", that is in undiluted form. If the aminonitrile mixture is a solid or contains solid at room temperature, it may be dissolved or suspended in sufficient alcohol to facilitate delivery to the reaction mass.

In the preferred embodiment of this invention, the aqueous sodium hypochlorite solution and the aminonitrile mixture are added simultaneously with stirring to the cold alcohol. The molar ratio of the sodium hypochlorite to the aminonitrile mixture is maintained in the range of 1.2 to 2.5 during the entire course of the addition. During the addition, the temperature of the reaction mixture should be held at or below 0° C. The reactants should be added at the maximum rate compatible with this temperature requirement. By-products can be minimized by decreasing the temperature as the addition time is shortened. In any event, addition times of 30 to 60 minutes appear optimum. When the addition of the reactants is complete, the temperature of the mixture is allowed to rise to between 5° and 10° C.

After heat evolution ceases, sufficient water is added at 5°–10° C. to adjust the alcohol/water ratio to 1 on a volume basis. At this ratio the sodium chloride (introduced with aqueous NaOCl solution and produced during the reaction) is dissolved, and most of the azo product separates as an upper layer. It can be isolated at this time. However, in order to insure the decomposition of any undesirable organic and/or inorganic oxidizing species which could severely contaminate the product, either before or after the water is added but before the azonitrile is isolated, the pH of the reaction mixture is adjusted to a maximum of 4, generally from 3 to 1 and preferably 2 to 1. A chemical reducing agent is then added.

Any acid or compound which will yield an acid in water may be used in the acidification step. For example, hydrochloric, sulfuric, phosphoric and the like acids may be used as well as sulfur dioxide, nitrogen dioxide and so on. Hydrochloric acid is preferred.

Any chemical reducing agent may be used. Generally, sulfur dioxide, nitrogen oxide, salts that dissociate in an aqueous medium to yield nitrate, sulfite, bisulfite, thiosulfate and the like anions, including sodium, potassium, lithium, quaternary amino, magnesium, calcium and the like salts of any of the above anions may be used. Organic compounds such as oxalic acid, formaldehyde, and hydroxylamine and the like may also be used although the inorganic chemical reducing agents are preferred. Mixtures of any of the reducing agents may also be used. Sulfur dioxide is a preferred reducing agent particularly where it is also used as the acidifying agent.

The amount of the chemical reducing agent is determined by titrating a sample of reaction mixture which has been added to an acidified potassium iodide solution with a solution of sodium thiosulfate, preferably 0.1 normal. The iodide reacts with the oxidants in the reaction mixture and becomes iodine. The thiosulfate reduces the iodine thus formed back to the iodide. The amount of reducing agent used is based upon equivalents or moles of oxidizing impurity present in the reaction mixture. Any amount of reducing agent from 1.0 to 2.0 or more equivalents per equivalent of oxidant present can be used although 1.0 to 1.25 equivalents of reducing agent per equivalent of oxidant is preferred.

While the invention has been described as yielding liquid mixtures of azonitriles when two aminonitrile starting materials are employed, it is also possible to prepare liquid azonitrile mixtures when more than two aminonitrile starting materials are used. As the number of aminonitrile starting materials is increased, there is a numerical increase in the number of symmetrical azonitriles produced and an exponential increase in the number of unsymmetrical azonitriles produced. With the increase in number of compounds and with the increase in weight proportion of lower melting unsymmetrical-to-symmetrical compounds, it is evident that liquid azonitrile mixtures will be highly favored as the number of aminonitriles is increased above two.

The invention is further illustrated but is not intended to be limited by the following examples in which all parts and percentages are by weight unless otherwise specified.

EXAMPLES OF LIQUID AZONITRILE PREPARATIONS

Illustrative Procedure for Preparing Aminonitriles

Five moles of a ketone or a mixture of ketones is charged into a one liter pressure vessel. The vessel is cooled with dry ice and acetone to a temperature of about −35° C. and 5–10 grams of ammonia and five moles (135 g.) of hydrogen cyanide are introduced in sufficiently small portions to avoid raising the temperature in the vessel. The vessel is closed, heated to room temperature (about 20° C.) and pressurized to 50 p.s.i. with ammonia. The reaction mixture is then heated at 40° C. for 8 hours while the ammonia pressure is maintained at 50 p.s.i.

The vessel is then cooled to room temperature and the contents discharged.

In this manner aminonitriles are obtained at yields of 85–97 percent as illustrated in the following Table:

TABLE I

| Ketone | Aminonitrile(s) | Yield Aminonitrile(s) % |
| --- | --- | --- |
| Methyl Ethyl | 2-amino-2-methylbutyronitrile | 85–90 |
| Methyl n-Butyl | 2-amino-2-methylhexanonitrile | 88–92 |
| Methyl n-Amyl | 2-amino-2-methylheptanonitrile | 90–95 |
| Methyl Ethyl-/Methyl n-Butyl | 2-amino-2-methylbutyronitrile/ 2-amino-2-methylhexanonitrile | 85–90.5 |
| Methyl Ethyl-/Methyl n-Amyl | 2-amino-2-methylbutyronitrile/ 2-amino-2-methylheptanonitrile | 90–93.5 |

EXAMPLE 1

Six hundred grams of an equimolar mixture of 2-amino-2-methylbutyronitrile and 2-amino-2-methylhexanonitrile prepared from equimolar amounts of methyl ethyl and methyl n-butyl ketones as described above contained 4.55 moles of the aminonitriles. The mixture was purged with air for 1 hour to remove ammonia before being used.

Eight and one-half liters of absolute methanol were charged into a 30 liter glass-lined metal reactor equipped with a temperature measuring device, motor-driven multi-blade stirrer and liquid addition inlet ports. The reactor was jacketed for cooling with a circulated dry ice-acetone mixture and the methanol in the reactor was cooled to −10° C. With rapid stirring, the aminonitrile mixture and 4.06 kg. of a 15.0 percent solution of sodium hypochlorite in water were added simultaneously to the reactor through ports at rates such that the additions were completed simultaneously in 1 hour. The molar ratio of NaOCl to aminonitrile was 1.8. Stirring and cooling were continued for 10 minutes, after which the reaction mixture was allowed to warm to 10° C., which temperature was maintained for 15 minutes. Over a ten minute time span, about 5.7 l. of water, cooled to 10° C. were added to the mixture.

In order to decompose undesirable organic and inorganic oxidizing species which would otherwise severely contaminate the azonitrile product, in particular, organic nitrogen chloride compounds, the reaction mixture was acidified to a pH of 2.0 with hydrochloric acid and a solution of 190 g. of sodium bisulfite in 1.3 l. water, also acidified to a pH of 2.0, was added. The mixture was rapidly stirred for 15 minutes.

On standing, the mixture separated into two phases. The upper layer of liquid product was separated, and washed with a 10% aqueous sodium bicarbonate solution, then with water, and then dried over anhydrous sodium sulfate. A test with acidified potassium iodide showed no oxidizing species to be present.

The product, a pale yellow liquid of low viscosity, weighed 450 g. An assay of the liquid for azonitrile content showed the product to be 90% pure so that the yield was 81%. The azonitrile composition was a mixture of two symmetrical azonitriles, 2,2′-azobis(2-methylbutyronitrile) and 2,2′-azobis(2-methylhexanonitrile), and an unsymmetrical azonitrile, 2-[(1-cyano-1-methylpropyl)azo]-2-methylhexanonitrile, at a mole ratio of 1:1:2; it had a freezing range between −20° C. and −25° C.

This liquid product is highly effective as a catalyst for any ethylene polymerization including the production of high pressure (low density) polyethylene by conventional processes at concentrations of 0.005%, 0.01% and 1.0% by weight of the undiluted liquid product based on the weight of the ethylene polymerized. It also functions efficiently as an initiator for any ethylene copolymerization including the polymerization of ethylene and vinyl acetate (80/20), ethylene and methacrylic acid (90/10) and ethylene/methyl methacrylate/methacrylic acid (70/25/5) by conventional processes at a concentration of 0.1% based on the weight of the monomers.

EXAMPLES 2–7

Liquid 2,2′-azobis(2-methylbutyronitrile) C, 2,2′-azobis(2-methylhexanonitrile) D and 2-[(1-cyano-1-methylpropyl)azo]-2-methylhexanonitrile E mixtures were produced by reacting 2-amino-2-methylbutyronitrile A and 2-amino-2-methylhexanonitrile B prepared from methyl ethyl and methyl n-butyl ketones at varying ratios using the procedure described herein. The results are tabulated below:

TABLE II

| Example | Ratio A:B | Yield Azonitriles (%) | Freezing Range Azonitriles (° C) | Azonitrile Ratio C:D:E |
| --- | --- | --- | --- | --- |
| 2 | 2.5:1 | 60 | +25 to +15 | 6.3:1:5 |
| 3 | 2.0:1 | 72 | 0 to −10 | 4:1:4 |
| 4 | 1.5:1 | 70 | −12 to −20 | 2.3:1:3 |
| 5 | 1:1.5 | 72 | −12 to −20 | 1:2.3:3 |
| 6 | 1:2.0 | 68 | 0 to −10 | 1:4:4 |
| 7 | 1:2.5 | 65 | +25 to +15 | 1:6.3:5 |

The above liquid azonitrile products are efficient initiators for polymerizing ethylene under high pressure at concentrations of 0.005 to 1% by weight of the azonitrile mixture based on the weight of the monomer. The azonitrile products are used at concentrations of 10 to 85% by weight of the azonitrile mixture, diluted with hexane.

EXAMPLES 8–10

Liquid 2,2′-azobis(2-methylbutyronitrile) C, 2,2′-azobis(2-methylhexanonitrile) D, and 2-[(1-cyano-1-methylpropyl)azo]-2-methylhexanonitrile E mixtures were prepared as described in Example 1 except that the sodium hypochlorite:aminonitrile mole ratios were varied. The results are tabulated below:

TABLE III

| Example | Mole Ratio NaOCl:Aminonitrile | Yield Azonitriles (%) | Freezing Range Azonitriles (° C) | Azonitrile Ratio C:D:E |
| --- | --- | --- | --- | --- |
| 8 | 1.2:1.0 | 65 | −20 to −25 | 1:1:2 |
| 9 | 1.5:1.0 | 75 | −20 to −25 | 1:1:2 |
| 10 | 2.5:1.0 | 60 | −20 to −25 | 1:1:2 |

EXAMPLES 11–14

Liquid 2,2′-azobis(2-methylbutyronitrile) C, 2,2′-azobis(2-methylhexanonitrile) D and 2-[(1-cyano-1-methylpropyl)azo]-2-methylhexanonitrile E mixtures were prepared as described in Example 1 except that temperatures other than −10° C. were used in the conversion step. The results are tabulated below:

TABLE IV

| Example | Oxidative Conversion Temp. (°C) | Yield Azonitriles (%) | Freezing Range Azonitriles (°C) | Azonitrile Ratio C:D:E |
| --- | --- | --- | --- | --- |
| 11 | −25 | 62 | −20 to −25 | 1:1:2 |
| 12 | −15 | 70 | −20 to −25 | 1:1:2 |
| 13 | − 5 | 75 | −20 to −25 | 1:1:2 |
| 14 | 0 | 68 | −20 to −25 | 1:1:2 |

EXAMPLES 15–18

Liquid 2,2′-azobis(2-methylbutyronitrile) C, 2,2′-azobis(2-methylhexanonitrile) D and 2-[(1-cyano-1-methylpropyl)azo]-2-methylhexanonitrile E mixtures were prepared as described in Example 1 except that the addition times in the oxidative step were varied. The results are tabulated below:

TABLE V

| Example | Additive Time (Min.) | Yield Azonitriles (%) | Freezing Range Azonitriles (°C) | Azonitrile Ratio C:D:E |
| --- | --- | --- | --- | --- |
| 15 | 15 | 67 | −20 to −25 | 1:1:2 |
| 16 | 30 | 75 | −20 to −25 | 1:1:2 |
| 17 | 90 | 74 | −20 to −25 | 1:1:2 |
| 18 | 120 | 73 | −20 to −25 | 1:1:2 |

EXAMPLES 19–27

Liquid azonitriles were produced from equimolar two-aminonitrile mixtures by the procedure described in Example 1 and the results are tabulated below:

TABLE VI

| Example | Aminoitrile System | Products | Product Freezing Range (°C) | Azonitrile Ratio C:D:E |
| --- | --- | --- | --- | --- |
| 19 | 2-amino-2-methylbutyronitrile<br>2-amino-2-methylheptanonitrile | C 2,2′-azobis(2-methylbutyronitrile)<br>D 2,2′-azobis(2-methylheptanonitrile)<br>E 2-[(1-cyano-1-methylpropyl)azo]-2-methylheptanonitrile | −20 to −25 | 1:1:2 |
| 20 | 2-amino-2-methylbutyronitrile<br>2-amino-2-ethylhexanonitrile | C 2,2′-azobis(2-methylbutyronitrile)<br>D 2,2′-azobis(2-ethylhexanonitrile)<br>E 2-[(1-cyano-1-methylpropyl)azo]-2-ethylhexanonitrile | −20 to −25 | 1:1:2 |
| 21 | 2-amino-2-methylbutyronitrile<br>2-amino-2-ethylheptanonitrile | C 2,2′-azobis(2-methylbutyronitrile)<br>D 2,2′-azobis(2-ethylheptanonitrile)<br>E 2-[(1-cyano-1-methylpropyl)azo]-2-ethylheptanonitrile | −20 to −25 | 1:1:2 |
| 22 | 2-amino-2-methylbutyronitrile<br>2-amino-2-methyloctanonitrile | C 2,2′-azobis(2-methylbutyronitrile)<br>D 2,2′-azobis(2-methyloctanonitrile)<br>E 2-[(1-cyano-1-methylpropyl)azo]-2-methyloctanonitrile | − 5 to −15 | 1:1:2 |
| 23 | 2-amino-2-methylhexanonitrile<br>2-amino-2-methyloctanonitrile | C 2,2′-azobis(2-methylhexanonitrile)<br>D 2,2′-azobis(2-methyloctanonitrile)<br>E 2-[(1-cyano-1-methylpentyl)azo]-2-methyloctanonitrile | − 5 to −15 | 1:1:2 |
| 24 | 2-amino-2-methylpentanonitrile<br>2-amino-2-ethylhexanonitrile | C 2,2′-azobis(2-methylpentanonitrile)<br>D 2,2′-azobis(2-ethylhexanonitrile)<br>E 2-[(1-cyano-1-methylbutyl)azo]-2-ethylhexanonitrile | − 5 to −15 | 1:1:2 |
| 25 | 2-amino-2-methylpentanonitrile<br>2-amino-2-ethylheptanonitrile | C 2,2′-azobis(2-methylpentanonitrile)<br>D 2,2′-azobis(2-ethylheptanonitrile)<br>E 2-[(1-cyano-1-methylbutyl)azo]-2-ethylheptanonitrile | − 5 to −15 | 1:1:2 |
| 26 | 2-amino-2-methylhexanonitrile<br>2-amino-2-methylheptanonitrile | C 2,2′-azobis(2-methylhexanonitrile)<br>D 2,2′-azobis(2-methylheptanonitrile)<br>E 2-[(1-cyano-1-methylpentyl)azo]-2-methylheptanonitrile | +20 to +10 | 1:1:2 |
| 27 | 2-amino-2-methylpentanonitrile<br>2-amino-2-methyloctanonitrile | C 2,2′-azobis(2-methylpentanonitrile)<br>D 2,2′-azobis(2-methyloctanonitrile)<br>E 2-[(1-cyano-1-methylbutyl)azo]-2-methyloctanonitrile | +20 to +10 | 1:1:2 |
| 28 | 2-amino-2-methylpentanonitrile<br>2-amino-2-methylhexanonitrile | C 2,2′-azobis(2-methylpentanonitrile)<br>D 2,2′-azobis(2-methylhexanonitrile)<br>E 2-[(1-cyano-1-methylbutyl)azo]-2-methylhexanonitrile | +20 to +10 | 1:1:2 |
| 29 | 2-amino-2-methylpentanonitrile<br>2-amino-2-methylheptanonitrile | C 2,2′-azobis(2-methylpentanonitrile)<br>D 2,2-azobis(2-methylheptanonitrile)<br>E 2-[(1-cyano-1-methylbutyl)azo]-2-methylheptanonitrile | +20 to +10 | 1:1:2 |
| 30 | 2-amino-2-methylhexanonitrile<br>2-amino-2-ethylheptanonitrile | C 2,2′-azobis(2-methylhexanonitrile)<br>D 2,2′-azobis(2-ethylheptanonitrile)<br>E 2-[(1-cyano-1-methylpentyl)azo]-2-ethylheptanonitrile | +20 to +10 | 1:1:2 |

All of the azonitrile mixtures of the foregoing examples are useful as polymerization catalysts such as, for example, for the polymerization of ethylene under high pressure. The products having freezing points of −20° to −30° C. can be used full strength or diluted. The products having a freezing point of 0 to −20° C. can be used full strength, particularly those having a freezing point closer to −20° C. but they are preferably diluted, with a suitable solvent. The products having a freezing point of +25° to 0° C. are generally diluted more extensively for use rather than being used full strength.

In the following examples, the unique nature of the instant invention is graphically illustrated. Mixtures of aminonitriles at a molar ratio of 1:1 are reacted to yield mixtures of azonitriles at a molar ratio of C:D:E of 1:1:2. In every case, the product was a solid. A comparison of these products with those obtained by the practice of this invention as outlined in the previous examples illustrates the unique nature of the invention whereby liquid azonitrile mixtures are obtained.

TABLE VII

| Example | Aminonitrile System | Products | Melting Point (° C) |
|---|---|---|---|
| 31 | 2-amino-2-methylpropionitrile<br>2-amino-2-methylbutyronitrile | 2,2'-azobis(2-methylpropionitrile)<br>2,2'-azobis(2-methylbutyronitrile)<br>2-[(1-cyano-1-methylethyl)azo]-2-methylbutyronitrile | 86 |
| 32 | 2-amino-2-methylhexanonitrile<br>2-amino-2,5-dimethylhexanonitrile* | 2,2'-azobis(2-methylhexanonitrile)<br>2,2'-azobis(2,5-dimethylhexanonitrile)<br>2-[(1-cyano-1-methylpentyl)azo]2,5-dimethylhexanonitrile | 74 |
| 33 | 2-amino-2-methylpentanonitrile<br>2-amino-2,5-dimethylhexanonitrile* | 2,2'-azobis(2-methylpentanonitrile)<br>2,2'-azobis(2,5-dimethylhexanonitrile)<br>2-[(1-cyano-1-methylbutyl)azo]-2,5-dimethylhexanonitrile | 80 |

*Branch chain form.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as set forth in the claims.

What is claimed is:

1. Azonitrile mixture having a freezing point of a maximum of 25° C. selected from the group consisting of:
   A. 2,2'-azobis(2-methylbutyronitrile), 2,2'-azobis(2-methylhexanonitrile) and 2-[(1-cyano-1-methylpropyl)azo]-2-methylhexanonitrile;
   B. 2,2-azobis(2-methylbutyronitrile), 2,2'-azobis(2-methylheptanonitrile) and 2-[(1-cyano-1-methylpropyl)azo]-2-methyl-heptanonitrile;
   C. 2,2'-azobis(2-methylbutyronitrile), 2,2'-azobis(2-ethylhexanonitrile) and 2-[(1-cyano-1-methylpropyl)azo]-2-ethylhexanonitrile;
   D. 2,2'-azobis(2-methylbutyronitrile), 2,2'-azobis(2-ethylheptanonitrile) and 2-[(1-cyano-1-methylpropyl)azo]-2-ethylheptanonitrile;
   E. 2,2'-azobis(2-methylbutyronitrile), 2,2'-azobis(2-methyloctanonitrile) and 2-[(1-cyano-1-methylpropyl)azo]-2-methyloctanonitrile;
   F. 2,2'-azobis(2-methylpentanonitrile), 2,2'-azobis(2-ethylhexanonitrile) and 2-[(1-cyano-1-methylbutyl)azo]-2-ethylhexanonitrile;
   G. 2,2'-azobis(2-methylhexanonitrile), 2,2'-azobis(2-methyloctanonitrile) and 2-[(1-cyano-1-methylpentyl)azo]-2-methyloctanonitrile;
   H. 2,2'-azobis(2-methylpentanonitrile), 2,2'-azobis(2-ethylheptanonitrile) and 2-[(1-cyano-1-methylbutyl)azo]-2-ethylheptanonitrile;
   I. 2,2'-azobis(2-methylhexanonitrile), 2,2'-azobis(2-methylheptanonitrile) and 2-[(1-cyano-1-methylpentyl)azo]-2-methylheptanonitrile;
   J. 2,2'-azobis(2-methylpentanonitrile), 2,2'-azobis(2-methyloctanonitrile) and 2-[(1-cyano-1-methylbutyl)azo]-2-methyloctanonitrile;
   K. 2,2'-azobis(2-methylpentanonitrile), 2,2'-azobis(2-methylhexanonitrile) and 2-[(1-cyano-1-methylbutyl)azo]-2-methylhexanonitrile;
   L. 2,2'-azobis(2-methylpentanonitrile), 2,2'-azobis(2-methylheptanonitrile) and 2-[(1-cyano-1-methylbutyl)azo]-2-methylheptanonitrile; and
   M. 2,2'-azobis(2-methylhexanonitrile), 2,2'-azobis(2-ethylheptanonitrile) and 2-[(1-cyano-1-methylpentyl)azo]-2-ethylheptanonitrile.

2. The mixture of claim 1 having a freezing point below −20° C. selected from the group consisting of
   A. 2,2'-azobis(2-methylbutyronitrile), 2,2'-azobis(2-methylhexanonitrile) and 2-[(1-cyano-1-methylpropyl)azo]-2-methylhexanonitrile;
   B. 2,2-azobis(2-methylbutyronitrile), 2,2'-azobis(2-methylheptanonitrile) and 2-[(1-cyano-1-methylpropyl)azo]-2-methylheptanonitrile;
   C. 2,2'-azobis(2-methylbutyronitrile), 2,2'-azobis(2-ethylhexanonitrile) and 2-[(1-cyano-1-methylpropyl)azo]-2-ethylhexanonitrile;
   D. 2,2'-azobis(2-methylbutyronitrile), 2,2'-azobis(2-ethylheptanonitrile) and 2-[(1-cyano-1-methylpropyl)azo]-2-ethylheptanonitrile.

3. The mixture of claim 1 having a freezing point from 0° C. to −20° C. selected from the group consisting of
   E. 2,2'-azobis(2-methylbutyronitrile), 2,2'-azobis(2-methyloctanonitrile) and 2-[(1-cyano-1-methylpropyl)azo]-2-methyloctanonitrile;
   F. 2,2'-azobis(2-methylpentanonitrile), 2,2'-azobis(2-ethylhexanonitrile) and 2-[(1-cyano-1-methylbutyl)azo]-2-ethylhexanonitrile;
   G. 2,2'-azobis(2-methylhexanonitrile), 2,2'-azobis(2-methyloctanonitrile) and 2-[(1-cyano-1-methylpentyl)azo]-2-methyloctanonitrile,
   H. 2,2'-azobis(2-methylpentanonitrile), 2,2'-azobis(2-ethylheptanonitrile) and 2-[(1-cyano-1-methylbutyl)azo]-2-ethylheptanonitrile.

4. The mixture of claim 1 having a freezing point from 25° C. to 0° C. selected from the group consisting of:

I. 2,2'-azobis(2-methylhexanonitrile), 2,2'-azobis(2-methylheptanonitrile) and 2-[(1-cyano-1-methylpentyl)azo]-2-methylheptanonitrile,
J. 2,2'-azobis(2-methylpentanonitrile), 2,2'-azobis(2-methyloctanonitrile) and 2-[(1-cyano-1-methylbutyl)azo]-2-methyloctanonitrile;
K. 2,2'-azobis(2-methylpentanonitrile), 2,2'-azobis(2-methylhexanonitrile) and 2-[(1-cyano-1-methylbutyl)azo]-2-methylhexanonitrile,
L. 2,2'-azobis(2-methylpentanonitrile), 2,2'-azobis(2-methylheptanonitrile) and 2-[(1-cyano-1-methylbutyl)azo]-2-methylheptanonitrile,
M. 2,2'-azobis(2-methylhexanonitrile), 2,2'-azobis(2-ethylheptanonitrile) and 2-[(1-cyano-1-methylpentyl)azo]-2-ethylheptanonitrile.

* * * * *

UNITED STATES PATENT OFFICE
CERTIFICATE OF CORRECTION

PATENT NO. : 3,987,025
DATED : OCTOBER 19, 1976
INVENTOR(S) : EARL P. MOORE, JR.

It is certified that error appears in the above–identified patent and that said Letters Patent are hereby corrected as shown below:

In the ABSTRACT, I., after "(2-methylhexanonitrile," and before the comma add -- ) --.

Column 3, line 64, after "1:1" insert -- to --.

Column 6, line 64, "expanse" should be -- expense --.

Column 7, line 32, after "with" insert -- the --.

Table VI, Example 29, D, after "2,2" insert -- ' --.

Signed and Sealed this twelfth Day of July 1977

[SEAL]

Attest:

RUTH C. MASON
*Attesting Officer*

C. MARSHALL DANN
*Commissioner of Patents and Trademarks*